United States Patent [19]

Nathans et al.

[11] Patent Number: 4,979,375
[45] Date of Patent: Dec. 25, 1990

[54] MAT FOR COOLING A PERSON DURING HOT WEATHER WITHOUT WETTING HAVING A LOW MANUFACTURING COST

[76] Inventors: Robert L. Nathans, 36 Stag Dr., Billerica, Mass. 01821; Walter C. Lovell, 348 Mountain Rd., Wilbraham, Mass. 01095

[21] Appl. No.: 255,276

[22] Filed: Oct. 11, 1988

[51] Int. Cl.⁵ ............................................. F25D 23/12
[52] U.S. Cl. ...................... 62/259.3; 5/422; 5/453; 128/400; 128/402
[58] Field of Search .............. 62/259.1, 259.3; 5/421, 5/422, 451, 453; 128/399, 400, 402, 403; 165/46

[56] References Cited

U.S. PATENT DOCUMENTS

| | | | |
|---|---|---|---|
| 2,726,658 | 12/1955 | Chessey | 62/259.3 |
| 3,610,323 | 10/1971 | Troyer | 62/259.3 |
| 4,114,620 | 9/1978 | Moore et al. | 5/421 X |
| 4,149,541 | 4/1979 | Gammons et al. | 5/421 X |
| 4,151,618 | 5/1979 | Carpenter | 5/421 X |
| 4,648,143 | 3/1987 | Breaux et al. | 5/421 X |
| 4,821,354 | 4/1989 | Little | 62/259.3 X |

Primary Examiner—Lloyd L. King
Attorney, Agent, or Firm—Robert L. Nathans

[57] ABSTRACT

Method and apparatus for enabling a person to relax and enjoy the outdoors on a hot humid day, without being continuously exposed to water which is uncomfortable for many people. A thin flexible cooling mat is positioned upon a lounge chair or is placed flat on the ground or worn in the manner of a vest. Ordinary tap water circulates through the mat, and since the water is supplied from a conventional in ground supply main having a substantially lower temperature than the air, the person's body, in direct contact with the mat, will be kept cool. The cooling water may irrigate the backyard at the same time. Since an entire family can relax while being cooled in their back yard, air conditioners will be turned off to save money, conserve electrical power, and thus reduce atmospheric pollution.

22 Claims, 3 Drawing Sheets

MAT FOR COOLING A PERSON DURING HOT WEATHER WITHOUT WETTING HAVING A LOW MANUFACTURING COST

BACKGROUND OF THE INVENTION

The present invention relates to the field of cooling devices and methods.

Enormous numbers of people suffer substantially during hot summer weather, and spend many unhappy hours indoors beside their air conditioners, if they can afford one or two of them. The cost of electricity to run the air conditioners must be added to the cost of a limited number of such air conditioners. The noise produced by them, day after day, and the feeling of being cooped up inside is unpleasant and people would often prefer relaxing out doors in their backyards. However, the heat from the sun and the hot air deters them from doing so.

Even if a family can afford a swimming pool, there is a need to lounge outdoors, away from air conditioners, and out of contact with the water for long periods of time, particularly for people who are no longer children or teenagers. For the vast majority who cannot afford a swimming pool, some common stopgap measures involve running under the lawn sprinkler, or splashing about in a wading pool. Since most people would like to be able to read or converse while relaxing out of doors, without being continually wetted, which becomes uncomfortable after awhile, what is really needed is a simple and inexpensive way to cool the body in a dry comfortable manner without direct contact with water.

Furthermore, as the atmosphere becomes more polluted, pressures will increase to reduce such pollution by reducing discharges of smoke and gas into the air. Such measures will in turn increase the cost, and the need to conserve electricity. For this reason also, it is desirable to provide for dry cooling of the body during hot summer weather over substantial time periods, while at the same time completely eliminating the use of electrical devices such as air conditioners which consume substantial electrical power.

SUMMARY OF PREFERRED EMBODIMENTS OF THE INVENTION

The above stated goals of increasing the comfort of people outdoors during hot summer weather, without continuously wetting the body, through the use of apparatus which has a low manufacturing cost and consumes no electrical power, are met by providing a thin flexible mat having a parallel array of enclosed cooling water conduits positioned just under major surface portions of the mat which is in direct contact with the body, to maximize the cooling effect. The water circulating through the mat is propelled into the cooling mat from a conventional pre-pressurized in ground water supply main which is far cooler than the surrounding air, and thus, in contrast with the use of an air conditioner, costs the user virtually nothing. Also, since the water ejected from the water main is always supplied under substantial pressure, the need for an electrical pump is also eliminated, so that no costly electrical power is consumed by the method of the invention. The degree of cooling for a plurality of mats, for cooling an entire family, may be precisely controlled via the conventional in place garden hose supply faucet coupled to the in ground water main, and as an added bonus, the water may be also used to sprinkle a lawn or garden at the same time. The flexible mat may be laid over a lounge chair, placed flat on the ground, or even be fastened to the body in the manner of a vest.

A simple and reliable pressure relief valve rubber band arrangement prevents the blockage of cooling water through the mat should the garden hose be kinked or have a shut off nozzle. The parallel mat cooling channel array prevents pinching of major portions of the conduit array, otherwise potentially causing cool water blockage, should the weight of a particularly heavy person be concentrated upon minor portions of the mat. Inflatable cushion embodiments of the invention containing cooling water conduits, may also be provided to eliminate the optional use of a comfort cushion positioned under the mat.

BRIEF DESCRIPTION OF THE DRAWINGS

Other objects, features and advantages of the present invention will become apparent upon study of the following description taken in conjunction with the drawings in which.

DETAILED DESCRIPTION OF PREFERRED EMBODIMENTS OF THE INVENTION

Figure 1:
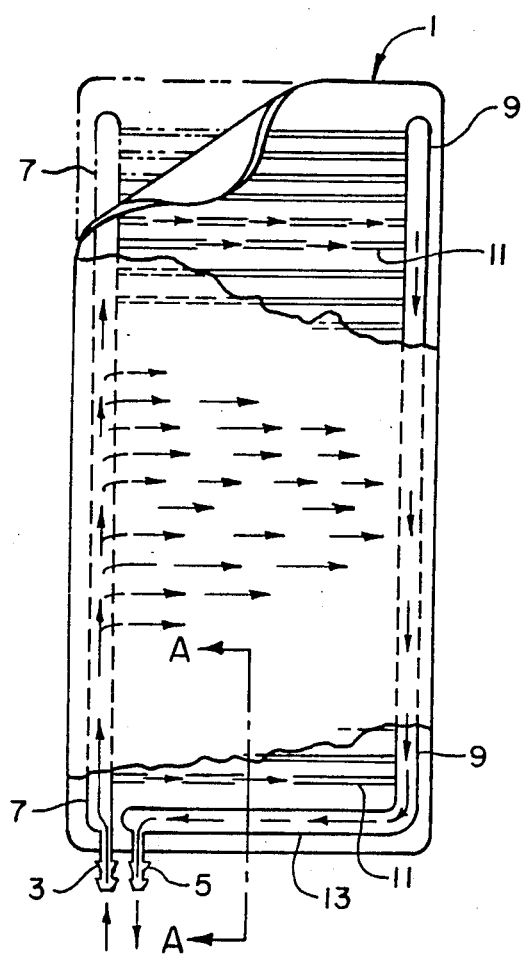
FIG. 1 discloses a plan view of the preferred mat.
Figure 2:
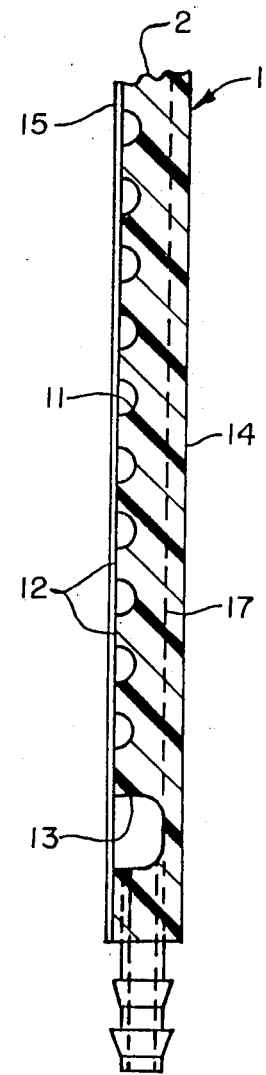
FIG. 2 discloses a sectional view taken through a portion of FIG. 1.

As shown in FIGS. 1 and 2, water inlet feed nipple 3 supplies water to an array of fully enclosed heat exchange channels 11 via inlet feed channel 7. Channels 11 are coupled in parallel between inlet feed channel 7 and output water drainage channel 9 coupled in turn to drainage nozzle 5. Figure two taken along sectional line A—A indicates that the inlet feed channel 7, (as shown by 17), and drainage channel 9 with its exit portion 13, are deeper than channels 11 to help prevent concentration of a persons body weight thereon from pinching off the flow of water through the cooling mat. Thus, nipple 3 and inlet channel 7 comprise an inlet water feed means and drainage channels 9 and 13, together with outlet nipple 5 comprise an outlet water drainage means.

The mat configuration illustrated, if made of moldable 0.25 inch thick plastic, would deter flow blocking channel pinch off, due to the lands 12 formed between channels 11, which support the weight of the person upon mat 1. With certain pliable mat materials and shallower channel configurations however, pinch off could become a problem, particularly if a very heavy person should sit on the mat. Thus channels 11 are coupled in parallel between channels 7 and 9; should a few of channels 11 become pinched off due to weight concentration upon minor portions of the mat 1, cooling water will continue to flow through the remaining major portions of the mat.

Figure 7:
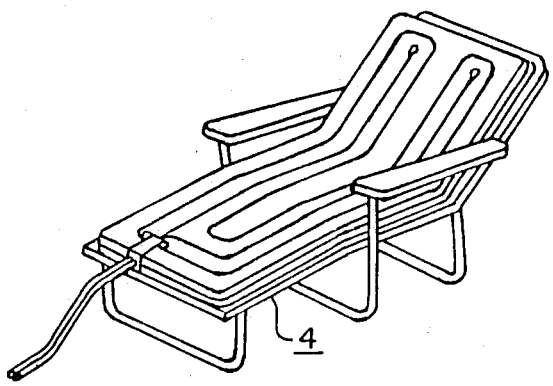
FIG. 7 illustrates a cooling mat positioned upon a lounge chair.

The mat substrate 2 could be made of moldable vinyl plastic for example, to enable easy forming of the flow conduits in a surface portion of the substrate. A plastic cover sheet 15, substantially thinner than the substrate, is thereafter laminated to the substrate by the application of heat and pressure using techniques well known to those versed in the art of plastic lamination. The preferred mat thickness is about 0.50 or less and could have a thickness of as little as about 0.10 inches, and would be flexible to enable it to conform to any desired surface such as lounge chair 4 of FIG. 7.

Figure 8:
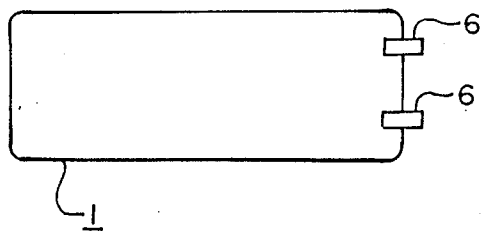
FIG. 8 illustrates a small mat which can be fastened to the body and worn in the manner of a vest.

As shown in FIG. 2, the fully enclosed channels 11 are just under the first face of the mat defined by thin cover sheet 15, and are substantially away from the second opposite face of the mat 14. As shown in FIG. 2, cooling channels 11 to be filled with water intersect and extend from a first major surface portion of substrate 2 and extend less than halfway through the thickness of the substrate. This arrangement maximizes conduction of heat from the person's body in direct contact with sheet 15. If the mat 1 were made sufficiently small and thin, and have "Velcro" touch-adhere type fasteners 6 thereon, as illustrated in FIG. 8, it could be worn about a person's body in the manner of a vest. Larger versions would of course be used for lounge chairs and horizontal placement on the ground.

Figure 3:
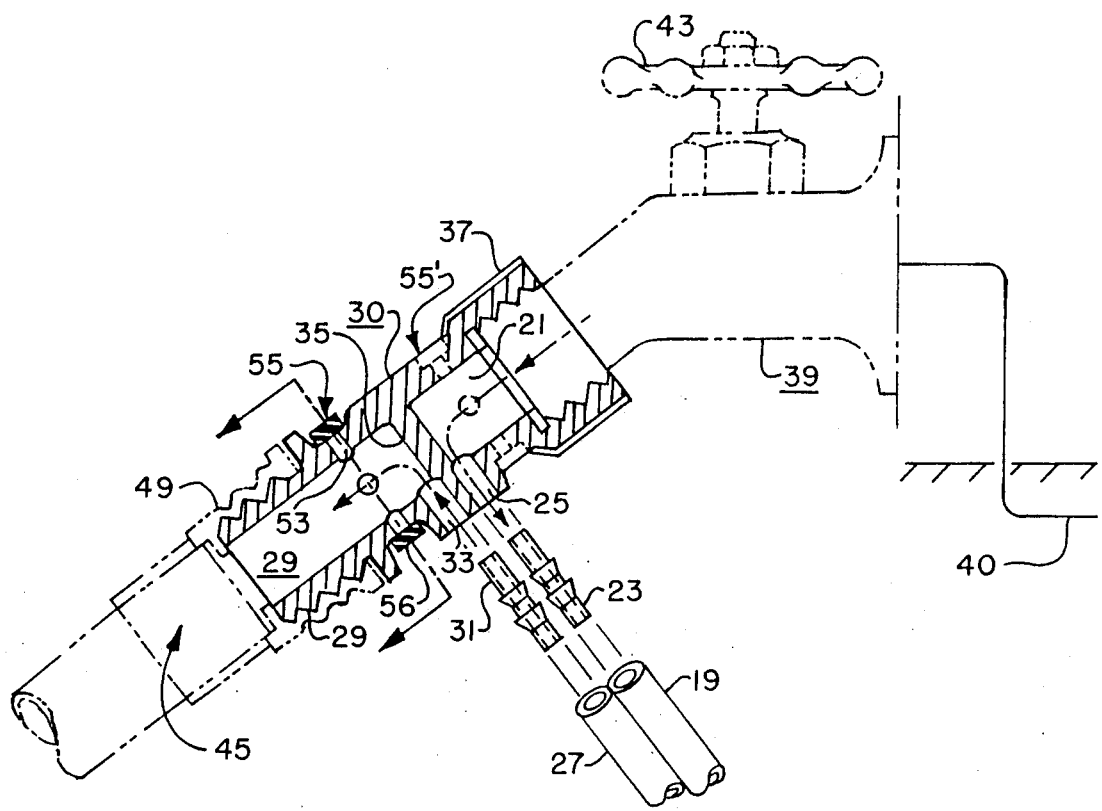
FIG. 3 illustrates a preferred flow diverter.

Inlet feed nipple 3 is coupled to flow diverter 30 of FIG. 3 via inlet hose 19, coupler 23 and channel 25 which receives coupler 23 fitted therein. Wall mounted faucet 39 is fed by the conventional pre-pressurized in ground water supply main 40. Faucet 39 is virtually always present to enable watering of the yard. Flow diverter water inlet chamber 21 is coupled to faucet 39 via screw coupler 37. Upon the rotation of the conventional faucet handle 43, water flows through inlet chamber 21 and into mat 1.

Mat outlet or drainage nipple 5 is preferably coupled to flow diverter outlet chamber 29, via flexible tube 27, coupler 31, and coupler reception section 33. Barrier 35 separates the inlet and outlet flow diverter chambers from each other. Advantageously, garden hose 45 may be screwed to the flow diverter outlet chamber via coupler component 49, to enable the cooling water to also irrigate an area of the backyard or to transport the water to an appropriate drainage area.

The aforesaid apparatus thus causes cool water from the conventional in ground water main feeding faucet 39 to draw heat directly from a persons body by conduction through the thin wall or cover sheet 15, covering major surface portions of the mat, to provide for efficient heat transfer. Thus the cool water conduits 11 are preferably formed just under surface portions of the mat, although this is not an absolute requirement since the flow rate of water may be increased by the further opening of faucet 39, to in turn increase the rate of heat transfer. During humid and hot days when the temperature was over ninety degrees, an ordinary plastic "Zip Lock" sandwich bag of thin wall plastic was filled with tap water and placed upon the chest. Due to the thin wall of the bag and the relatively cool temperature of the water drawn through the in ground supply main 40, the cooling effect was readily apparent.

Figure 4:
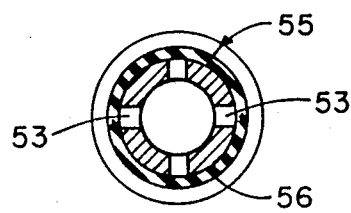
FIG. 4 is a sectional view taken through the valve portion of the flow diverter.

Should garden hose 45 become kinked, or its outlet nozzle closed, a pressure relief valve deters the stoppage of water flow through the mat. This relief valve 55 shown in FIGS. 3 and 4, consists of passageways 53, which pass completely through diverter outlet chamber 29, and a flat annular rubber band 56. As the water pressure within the diverter and hence within the mat conduits exceeds a given high level due to hose blockage, the band becomes displaced from passageways 53 and water is thus expelled from the apparatus. This valve thus relieves pressure in a simple and reliable manner, and may optionally be employed additionally in the inlet diverter chamber at 55' to prevent buildup in pressure in the mat conduits not caused by hose blockage. While water pressure buildup should not burst the thin overlay mat conduit cover sheet 15, of the embodiment of the invention of FIG. 2, it could possibly rupture other thin conduit walls of alternate designs such as a mat made of inflatable sections as shown in FIG. 6.

Figure 6:
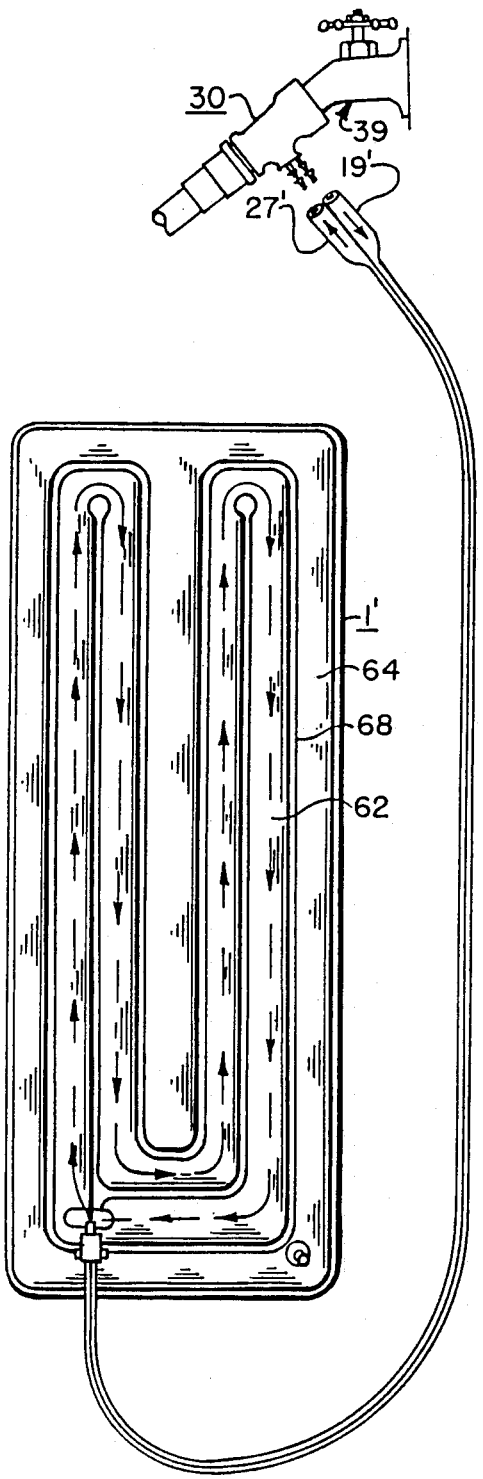
FIG. 6 illustrates a cooling mat having inflatable portions therein.

As shown in FIG. 6, cooling water is circulated through a centrally located cooling channel 62 which is surrounded by inflatable compartment 64, coupled to channel 62 via webbing sections 68. Inlet feed tube 19' and outlet drainage tube 27' coupled to flow diverter 30 provide the cooling water to the mat as described above. This embodiment of the invention provides considerable comfort, in contrast to the embodiment described above, which often would call for the use of an additional pliable mat for comfort, unless the mat was placed upon a thick lawn or the like. The inflatable mat also may be floated in a swimming pool, and like the first described embodiment, could be manufactured cheaply.

Figure 5:
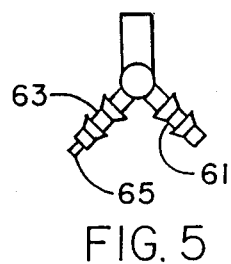
FIG. 5 illustrates a coupling device for supplying cooling water to two mats simultaneously.

Two mats may be simultaneously utilized by family members by providing distributor feed and drainage nipples such as the multiple pronged nipple member illustrated in FIG. 5, having nipple portion 61 for immediate use by one person. Should the family desire to buy an additional mat, hollow plug 65 is cut off with a knife or scissor to expose the hollow portion therein, and nipple 63 is connected to the input nipple 3 of the second mat by a flexible tube supplied therewith. A similar two pronged drainage nipple could be substituted for the straight drainage nipple 31, to enable drainage of both the first and second mat. Similar multiple nipple prong members for supplying water to three or four mats simultaneously would have additional hollow plug nipples, so that only one flow diverter design is required for expanded use of more mats. The two pronged nipple of FIG. 5 is very inexpensive and is available in the marketplace. In order to enable the most effective simultaneous use of such a plurality of mats, the flow rate of the water drawn from the in ground supply main is increased by turning faucet handle 43, to handle the added thermal load of additional mats put in use.

Thus the present invention teaches an economical method of cooling people during hot humid days, enabling them to enjoy the outdoors without being continuously subjected to direct contact with water, which is uncomfortable for many, and thus an entire family is able to read and converse in a comfortable relaxed manner. Since indoor air conditioner use will be substantially reduced, money will be saved, and conservation of energy will be effected, to in turn reduce pollution of the atmosphere. The apparatus is simple, has a low manufacturing cost and consumes no electrical power.

As embodiments of the invention other than those described above will readily occur to those skilled in the art, the scope of the invention is to be defined only by the terms of the following claims and art recognized equivalents thereof. For example the word "mat" is not to be interpreted in its narrowest sense, but is intended to include a water containing body such as the water cooling conduit cushion configuration of FIG. 6, provided such body would have a configuration so as to carry out the aforesaid objectives in a practical and economical manner. The water is passed through the mat on a "substantially continuous basis" which is intended to cover strictly continuous flow and intermittent flow which occurs often enough to effectively cool the person. Flow diverter 30 need not be directly connected to supply faucet 39. Should a family wish to locate the mats a substantial distance away from the house, a conventional garden hose would couple the supply faucet to the distant flow diverter located a few feet away from the mats. This permits supplying short standard lengths of the flexible tubes 19 and 27.

We claim:

1. Apparatus for cooling a person's body during hot seasons by utilizing water propelled from a conventional pre-pressurized in ground water supply main coupled to a water supply faucet comprising:

a mat having an inlet water feed means therein, means for coupling the inlet water feed means of said mat to said conventional pre-pressurized in ground water supply main via said water supply faucet as long as said apparatus is in use, an outlet water drainage means therein, and heat exchange water conduit means fully enclosed within said mat for drawing sufficient quantities of heat through a face of said mat from said person's body in direct contact with said mat by conduction and without the need to wet said body, means for coupling said heat exchange water conduit means between said inlet water feed means and said outlet water drainage means; and further including a flow diverter having a diverter water inlet chamber and a diverter water outlet chamber therein, first coupling means for coupling said diverter water inlet chamber to said water supply faucet coupled in turn to said conventional pre-pressurized in ground water supply main, second coupling means for coupling said diverter water inlet chamber to the inlet water feed means of said mat, and third coupling means for coupling the outlet water drainage means of said mat to said diverter water outlet chamber.

2. The apparatus of claim 1 including a garden hose coupler positioned adjacent said diverter water outlet chamber.

3. The apparatus of claim 1 including pressure relief valve means connected to said diverter water outlet chamber for enabling water to continue to flow through said mat even if a hose attached to the diverter water outlet chamber is impeding the flow of water through said hose.

4. The apparatus of claim 1 including pressure relief valve means positioned within said flow diverter comprising passageway means and an elastic member positioned over said passageway means for permitting water to flow through said passageway means when water pressure within said flow diverter exceeds a given pressure.

5. The apparatus of claim 4 wherein said elastic member comprises a substantially flat annular elastic band.

6. An inexpensive energy saving method of cooling a person's body during hot days without the need to wet said person's body comprising the steps of:

(a) providing a cooling mat having water inlet means and water outlet means together with water cooling conduit means coupled between said water inlet means and said water outlet means and fully enclosed within major portions of said mat for drawing heat from said person's body by conduction through said mat without the need to wet said body;

(b) directly utilizing only the reduced temperature of pre-pressurized water contained in a conventional pre-pressurized in ground water supply main relative to the elevated temperature of ambient air during hot days to cool said person's body by feeding said pre-pressurized water ejected from said in ground water supply main into the water inlet means of said mat; and (c) further including the step of coupling a lawn sprinkler to the water outlet means of said mat to enable said water to also be used to irrigate selected areas and thus not accumulate in one area.

7. The apparatus of claim 1 wherein said second coupling means includes a multiple pronged nipple member, at least one nipple member having a hollow plug therein for enabling said plug to be readily cut off, thereby to supply a second mat with cooling water when required.

8. Inexpensive cooling mat apparatus for cooling a person without wetting comprising:

(a) a cooling mat including a substrate having a predetermined thickness and a first major surface and a second opposite major surface, tubeless water conducting channels, formed within said substrate, intersecting and extending from said first major surface and positioned substantially away from said second major surface, for enhancing heat flow from said person into said tubeless water conducting channels, said channels being separated from each other by solid weight supporting lands of said substrate, coplanar with said first major surface, for supporting the weight of an adult person without pinching off said water conducting channels, a cover sheet for contacting said person, laminated to said first major surface of said substrate, said cover sheet having a thickness substantially less than the thickness of said substrate for further enhancing said heat flow from said person into said tubeless water conducting channels and for containing cooling water filling said channels so as not to wet said person; and (b) means for coupling said water conducting channels to an in ground water supply faucet for causing cooling water to flow through said tubeless water conducting channels.

9. The inexpensive cooling mat of claim 8 wherein said mat has an inlet water feed channel and an output water drainage channel and wherein the width of said mat is substantially less than the length thereof, and wherein said tubeless water conducting channels are each individually connected between said inlet water feed channel and said output water drainage channel and are parallel to said width to minimize temperature gradients across said mat.

10. The inexpensive cooling apparatus of claim 8 wherein said substrate is flexible, has a thickness of about one half inch or less, and wherein said tubeless water conducting channels extend less than halfway through the thickness of said substrate for enhancing heat flow from said person into said tubeless water conducting channels.

11. The inexpensive cooling apparatus of claim 9 wherein said substrate is flexible, has a thickness of about one half inch or less, and wherein said tubeless water conducting channels extend less than halfway through the thickness of said substrate to further maximize transfer of heat from said person into said tubeless water conducting channels.

12. The inexpensive cooling apparatus of claim 8 wherein said tubeless water conducting channels are molded into said substrate.

13. The inexpensive cooling apparatus of claim 9 wherein said tubeless water conducting channels are molded into said substrate.

14. The inexpensive cooling apparatus of claim 10 wherein said tubeless water conducting channels are molded into said substrate.

15. The inexpensive cooling apparatus of claim 11 wherein said tubeless water conducting channels are molded into said substrate.

16. An inexpensive cooling mat apparatus for cooling a person without wetting comprising:
    (a) a mat including a plurality of water conducting channels for conducting cooling water therethrough for cooling a person lying upon said mat without wetting, a plurality of inflatable compartments, coupling means for coupling said inflatable compartments and said water conducting channels together for maintaining said inflatable compartments and said water conducting channels side by side across major surface portions of said mat in a manner to enable said inflatable compartments to comfortably support the weight of said person to a sufficient degree to prevent pinchoff of said water conducting channels; and
    (b) means for coupling said water conducting channels to an in ground water supply faucet for causing cooling water to flow through said water conducting channels.

17. The cooling mat apparatus of claim 16 wherein said inflatable compartments substantially surround said water conducting channels.

18. The cooling mat apparatus of claim 16 wherein at least one of said inflatable compartments is centrally located upon said mat.

19. The cooling mat apparatus of claim 17 wherein at least one of said inflatable compartments is centrally located upon said mat.

20. The cooling mat apparatus of claim 16 wherein said coupling means comprises webbing sections for enabling said mat to be constructed of two sheets.

21. The cooling mat apparatus of claim 17 wherein said coupling means comprises webbing sections for enabling said mat to be constructed of two sheets.

22. The cooling mat apparatus of claim 18 wherein said coupling means comprises webbing sections for enabling said mat to be constructed of two sheets.

* * * * *